United States Patent
Falco

(10) Patent No.: US 7,743,771 B2
(45) Date of Patent: *Jun. 29, 2010

(54) EARPLUG WITH ARTICULATING STEM AND LOCKING FEATURES

(75) Inventor: Robert N. Falco, Indianapolis, IN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/584,326

(22) Filed: Oct. 20, 2006

(65) Prior Publication Data

US 2007/0102007 A1 May 10, 2007

Related U.S. Application Data

(63) Continuation-in-part of application No. 11/270,053, filed on Nov. 9, 2005.

(51) Int. Cl.
*A61F 11/00* (2006.01)
*H04R 25/00* (2006.01)

(52) U.S. Cl. .................. 128/864; 181/129; 381/380

(58) Field of Classification Search .......... 128/864–868; 181/128–130, 134, 135; 381/380, 71.1, 71.6
See application file for complete search history.

(56) References Cited

U.S. PATENT DOCUMENTS

| 5,074,375 | A  | * | 12/1991 | Grozil ................. 181/135 |
| 6,241,041 | B1 | * | 6/2001  | Leight ................. 181/135 |
| 2004/0129276 | A1 |   | 7/2004 | Kuno et al. |
| 2006/0162992 | A1 | * | 7/2006 | Seville ................. 181/135 |

FOREIGN PATENT DOCUMENTS

| WO | WO 9806363   | 2/1998 |
| WO | WO 9944556   | 9/1999 |
| WO | WO 2006078767 | 7/2006 |

OTHER PUBLICATIONS

Definition of Vertex.*
PCT Search Report—PCT/US2007/022421.

* cited by examiner

*Primary Examiner*—Patricia M Bianco
*Assistant Examiner*—Tarla R Patel
(74) *Attorney, Agent, or Firm*—Karl G. Hanson

(57) ABSTRACT

A hearing protection device is provided including a stem, a protrusion formed on the stem, an articulation point formed on the stem, and a sound attenuating element including a cavity, where the protrusion is disposed in locking engagement within the cavity to releasably attach the stem to the sound attenuating element, and where the stem is configured to at least partially articulate about the articulation point.

20 Claims, 10 Drawing Sheets

EARPLUG WITH ARTICULATING STEM AND LOCKING FEATURES

CROSS-REFERENCE TO RELATED APPLICATION

This application is a continuation in part of U.S. patent application Ser. No. 11/270,053 filed on 9 Nov. 2005, currently pending, the contents of which are incorporated by reference herein in their entirety.

TECHNICAL FIELD OF INVENTION

The invention concerns hearing protection devices and, more particularly, an earplug, and a stem for an earplug, where the stem includes a locking feature which facilitates assembly of the earplug and enables enhanced comfort to a wearer.

BACKGROUND OF INVENTION

The use of hearing protective and noise attenuating devices is well known, and various types of devices are available including, but not limited to, ear muffs, semi-aural devices, and earplugs. Earplugs are often preferred for their effectiveness in attenuating sound and for comfort properties provided thereby.

An earplug generally comprises a sound attenuating element which is placed in the ear canal of a wearer to occlude the canal and thus provide a desired sound attenuation. The sound attenuating element is commonly made of a compressible, resilient material such as a foam or a rubber.

The earplug may further include a stem extending from the sound attenuating element. The stem serves as a handle to facilitate general tactile manipulation of the earplug. Furthermore, the stem assists during insertion of the earplug into the earcanal by serving as a means for pushing the sound attenuating element to a sufficient depth within the earcanal. Correspondingly, the stem aids in removal of the earplug by providing a grip by which the earplug may be pulled from the earcanal.

The sound attenuating element and the stem of such earplugs may be formed separately and then fixed together or may be integrally formed together. In the case of the former, a rigid or semi-rigid stem is typically embedded partly or entirely within the resilient sound attenuating element. An adhesive is used to fix the stem to the attenuating element or the attenuating element may be formed directly on the stem so as to bond intimately therewith. In either case, manufacture and assembly can be a complicated, multi-step process, perhaps requiring numerous toolings, etc., and resulting in an overall increased cost of the earplug. Moreover, the stems for these types of earplugs are typically quite rigid so as to sustain being inserted within the sound attenuating element and bonded therein. While this relatively increased rigidity facilitates assembly of this traditional earplug, it detracts from the comfort provided thereby to the user by preventing or limiting the ability of the stem and earplug to conform to the natural curvature of the inner ear.

A conventional earplug having an integrally formed (i.e., one-piece) attenuating element and stem is typically pre-molded of a soft rubber-like material. This material is advantageous due to the comfort properties provided thereby. However, the soft rubber material lacks in rigidity and thus can be less effective for inserting the sounding attenuating element to a desired depth within the ear canal. Attempts at increasing the rigidity of the stem of this type of integrally formed earplug may be unsuccessful due to the corresponding stiffening of the sound attenuating element and hence the loss of comfort properties thereof. Some have attempted to add stiffening elements to the stem of integrally formed, pre-molded earplugs. However, this can be a complex assembly process and can result in an overall more expensive earplug. Moreover, the stiffening element is often too long relative to the axis of the earplug and thus cannot easily traverse the bend in the earcanal when inserted or is too short and thus does not properly serve the intended stiffening function.

Thus, an earplug is desired which includes a soft, comfortable sound attenuating element and a stem attached thereto for handling and inserting the earplug, where the stem is sufficiently rigid to enable insertion of the attenuating element to a desired earcanal depth and yet sufficiently pliable to remain comfortable within the ear and to allow the earplug to conform to the natural contours of the earcanal, and where the earplug is capable of being readily manufactured and assembled at a reasonable cost.

BRIEF SUMMARY OF THE INVENTION

The above discussed and other problems and deficiencies of the prior art are overcome or alleviated by the invention which provides a novel and nonobvious hearing protection device.

In one exemplary embodiment, the invention provides a hearing protection device including a stem, a protrusion formed on the stem, an articulation point formed on the stem, and a sound attenuating element including a cavity, where the protrusion is disposed in locking engagement within the cavity to releasably attach the stem to the sound attenuating element, and where the stem is configured to at least partially articulate about the articulation point.

The invention further provides a hearing protection device including an elongated stem member having an attachment portion and a handle portion, a protrusion formed on the attachment portion of the stem member, an area of reduced stem member cross-sectional area delimited by the attachment portion proximate to the protrusion, and a sound attenuating element including a cavity formed at an interior thereof, where the attachment portion is disposed within the cavity, where the protrusion is disposed within the cavity in locking engagement with a mating element of the sound attenuating element to releasably attach the stem member to the sound attenuating element, where the area of reduced stem member cross-sectional area delimits an articulation point of the stem member, and where the stem member and the sound attenuating element disposed thereon are configured to at least partially articulate about articulation point.

The above-discussed and other features and advantages of the apparatus and method of the invention will be appreciated and understood by those skilled in the art from the following drawings and detailed description.

BRIEF DESCRIPTION OF THE FIGURES

Referring now to the drawings wherein like elements are numbered alike in the several FIGURES.

DETAILED DESCRIPTION OF THE PREFERED EMBODIMENT

Figure 1:
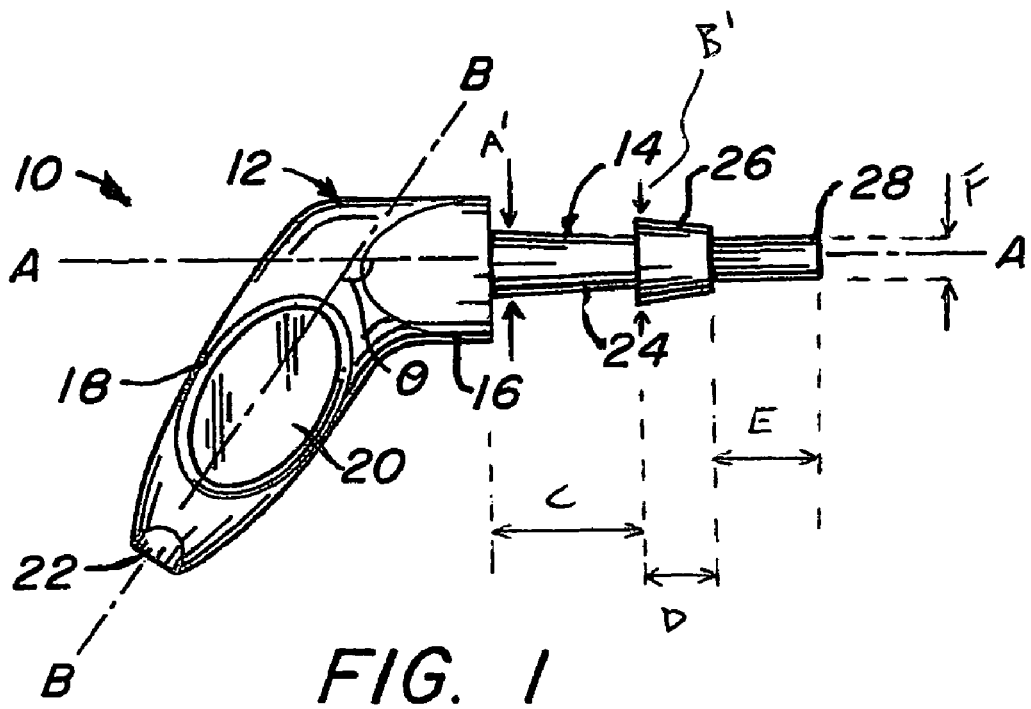
FIG. 1 is a side view of an earplug stem in one embodiment of the invention.
Figure 2:
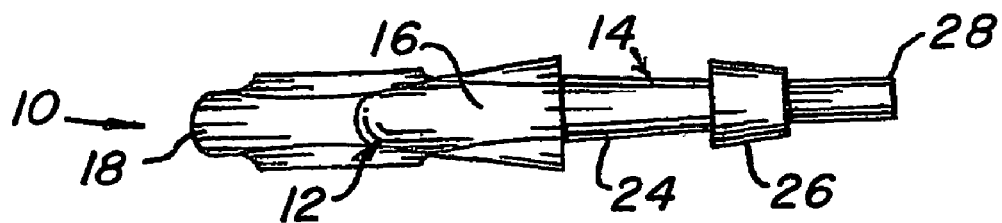
FIG. 2 is a top view thereof.
Figure 3:
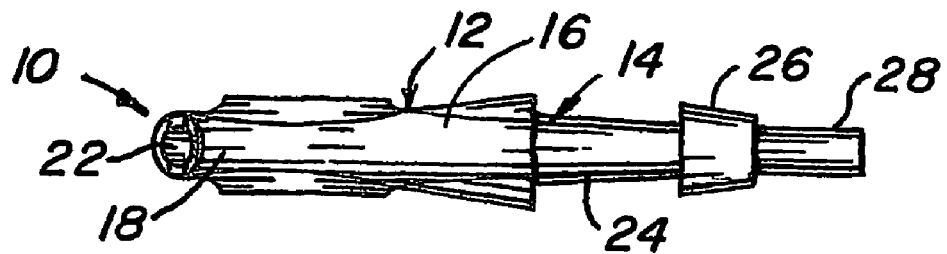
FIG. 3 is a bottom view thereof.
Figure 4:
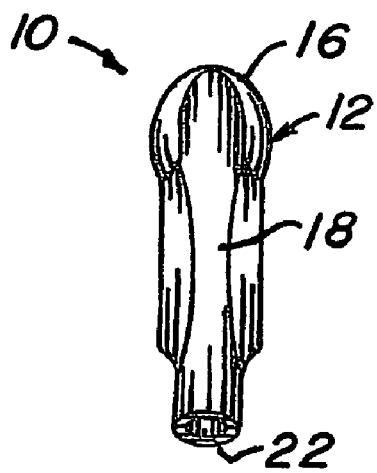
FIG. 4 is a rear view thereof.
Figure 5:
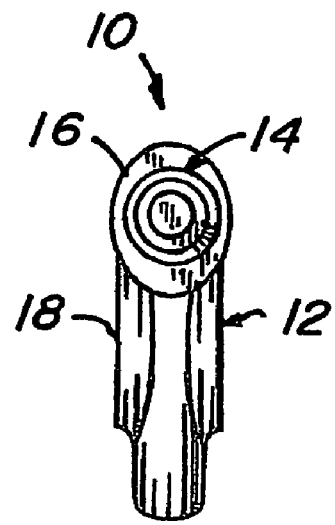
FIG. 5 is a front view thereof.
Figure 7:
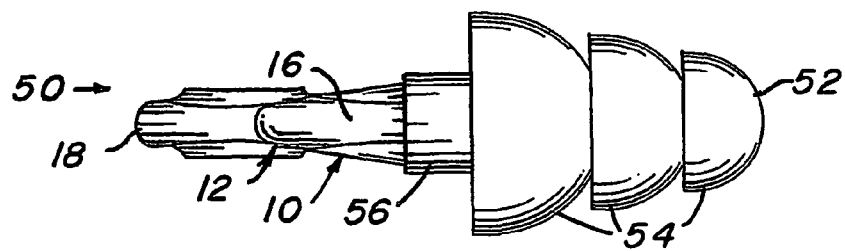
FIG. 7 is a top view thereof.
Figure 6:
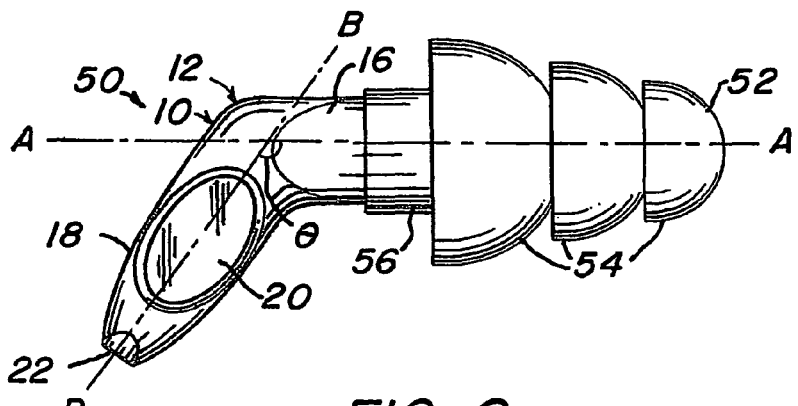
FIG. 6 is a side view of an earplug having the stem of FIGS. 1-5.
Figure 8:
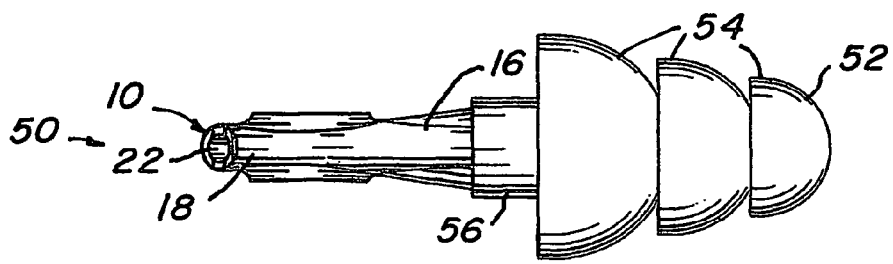
FIG. 8 is a bottom view thereof.
Figure 9:
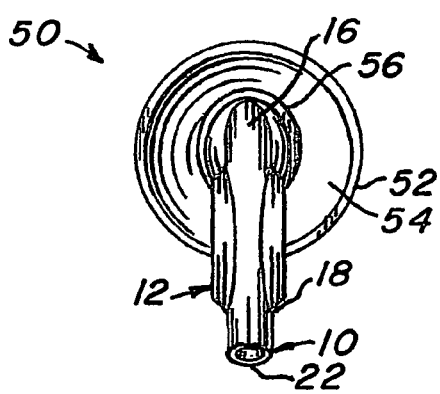
FIG. 9 is a rear view thereof.
Figure 10:
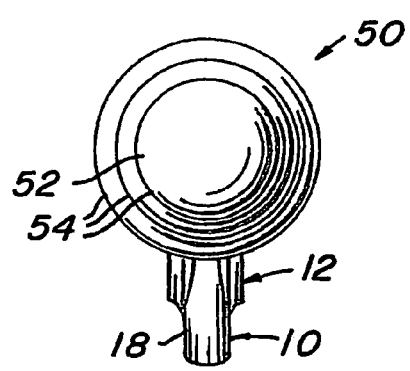
FIG. 10 is a front view thereof.

FIGS. 1-5 shows a stem 10 for an earplug 50 (see, FIGS. 6-10), in one exemplary embodiment of the invention. The stem 10 generally includes a handle portion 12 and a attachment portion 14 extending therefrom. As will be discussed herein in detail, the attachment portion 14 is particularly configured to include a locking feature which allows the stem 10 to be mated with a sound attenuating portion (see, FIGS. 6-10) of the earplug 50 without the use of adhesives, in situ molding processes, etc. The handle portion 12 is configured and oriented to facilitate handling, earcanal insertion, and earcanal removal of the earplug 10.

The handle portion 12 of the stem 10 includes a proximate portion 16 and an opposing distal portion 18. As shown in FIGS. 1-5, the proximate portion 16 is disposed near the attachment portion 14. The distal portion 18 is adjacent to the proximate portion 16, opposite from the attachment portion 14. The proximate portion 16 extends generally along an axis A-A shared with the attachment portion 14. (See, particularly, FIG. 1.) The distal portion 18 diverges from the proximate portion 16 along an axis B-B. The axis B-B is disposed at an angle θ relative to the axis A-A. The angle θ is generally greater than 90° and preferably between 110° and 140°. In the present exemplary embodiment, the angle θ is generally less than or equal to approximately 125°. In other words, in this exemplary embodiment, the axis B-B is not collinear with the axis A-A. Of course, this is merely illustrative. In another exemplary embodiment of the invention, the distal portion 18 may be collinear with the proximate portion 16. See, e.g., description below related to FIGS. 21-24.

In the illustrated embodiment, as mentioned, the distal portion 18 of the stem handle 12 extends at an angle θ relative to the proximate portion 16 and (as will be discussed further herein) relative to the attachment portion 14. The result is a substantially pistol-shaped stem 10. Due to this unique shape, the stem 10 may be advantageously worn by a wearer inconspicuously and in such manner so as to avoid inadvertent contact. That is, when an earplug utilizing the stem 10 is inserted into the ear of a wearer, the proximate portion 16 of the handle portion 12 extends slightly from the earcanal and the angled distal portion 18 extends in a downward direction from the earcanal and lies discretely in the folds of the outer ear and, particularly, in the tragus area of the ear. This allows the earplug to be worn discretely and disposes the handle portion 12 of the stem 10 in a region close to the ear and head of the wearer thus preventing against and minimizing inadvertent contact therewith.

Further advantageously, the angled stem 10 provides an angled handle portion 12 which is configured to be readily gripped, manipulated, and handled. The unique shape of the stem 10 further allows a wearer to twist the stem 10 upon inserting the earplug into the earcanal. That is, the angle formed in the stem 10 allows the wearer to exert sufficient torque to the earplug upon insertion into the earcanal such that the earplug, and the stem 10 particularly, may easily and comfortably traverse the natural bend of the earcanal thus properly disposing the sound attenuating element of the earplug within the earcanal to achieve sufficient occlusion.

The distal portion 18 of the stem handle 12 includes a handling area 20 disposed approximately midway along a length of the portion 18. The handling area 20 comprises a contoured surface for facilitating retention of the stem 10 between fingertips of the wearer. For example, the handling area 20 may comprise an oval shaped surface having planar and/or curvilinear features. That is, the handling area 20 may be flat, convex, concave, or any combination of these. The area 20 may additionally and/or alternatively include grip features which are disposed inset or in relief relative to the feature 20, such as score lines, protuberances, etc. The handling area 20 may further include indicia, symbols, etc., such as trade names, product names, etc. These may be printed at the handling area 20 or formed thereon in relief or in an inset fashion.

Figure 19:
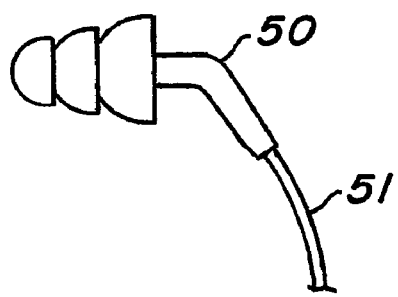
FIG. 19 is a side elevation view of an earplug according to FIGS. 6-10 having a cord attached thereto.

The distal portion 18, in the exemplary illustrated embodiment, includes an aperture 22 formed at an end opposite from the proximate portion 16. The aperture 22 extends along the axis B-B, forming a cavity within the distal portion 18. The aperture 22 and resulting cavity are generally circular in cross-section and are configured to receive and retain a cord 51 as shown in FIG. 19. The cord 51 allows the resulting earplug 50 to be attached to another earplug 50 to form a connected pair of earplugs 50. The cross-section of the aperture 22 may be sized slightly smaller than that of the cord 51 such that the cord is held therein in a friction fit. Additionally and/or alternatively, the cord 51 may be bonded to the distal portion 18 in the aperture by way of an adhesive agent, an in situ molding process, etc. Of course, the aperture 22 may be used to house any alternative device or element. For example, a detectable element such as a metallic or magnetic insert, may be disposed within the aperture.

As mentioned, the attachment portion 14 of the stem 10 includes important and novel features which facilitate attachment of the sound attenuating element 52 with the stem 10. In this exemplary embodiment, these features include a first conical portion 24 which has a generally serially decreasing circular cross-section and tapers toward a front of the attachment portion 14, and a second conical portion 26 adjacent to the portion 24 where the portion 26 also includes a serially decreasing circular cross-section which tapers in a direction toward the front of the attachment portion 14. The portion 14 also includes a front end 28 which is generally a cylindrical member extending away from the second conical portion 26. These features 24, 26, and 28 are specifically shaped, disposed, and configured to aid in affixing the sound attenuating element 52 to the stem 10. Namely, these features 24, 26, 28 include shapes, surfaces, and dimensions which are readily received and retained by the internal configuration of the sound attenuating element 52 to facilitate said affixation.

For example, in this exemplary embodiment, the first conical portion 24 includes a width A' proximate to the handle portion 12 of about 0.100 inch to about 0.150 inch and preferably about 0.125 inch. The first conical portion 24 tapers inwardly in a direction toward the front end 28 at an angle relative to a longitudinal axis of the first conical portion 24 of about 1 to 5 degrees and preferably of about 3 degrees. The first conical portion 24 generally includes a length C of about 0.250 inch to about 0.300 inch and is preferably about 0.275 inch. The second conical portion 26 includes a width B' of about 0.150 inch to about 0.200 inch and preferably of about 0.170 inch. The second conical portion 26 further includes a length D of about 0.120 inch to about 0.160 inch and preferably of about 0.145 inch. The second conical portion 26 tapers inwardly in a direction toward the front end 28 at an angle of about 5 to 15 degrees and preferably of about 8 degrees relative to a longitudinal axis of the portion 26. The front end 28 includes a longitudinal length of about 0.200 inch to about 0.250 inch and preferably of about 0.225 inch. A width F of the front end 28 is about 0.050 inch to about 0.100 inch and preferably about 0.080 inch. As shown in the drawings, in this exemplary embodiment, the front end 28 is generally a cylindrically shaped element which extends integrally from the second conical portion.

It is noted that the first conical portion 24 is not entirely conical but instead comprises a portion of a cone. That is, more accurately, the first conical portion 24 comprises a frustum of a cone where the frustum extends between the proximate portion 16 of the stem 10 and the second conical portion 26. Similarly, the second conical portion 26 is not a complete cone but instead is a frustum of a cone which extends from the first conical portion 24 to the front end 28. Thus, herein the portions 24 and 26 are referred to as "conical", but it shall be understood that in this one embodiment of the invention the first and second conical portions 24, 26 are actually frusta of respective cones.

Advantageously, the cross-section of the first conical portion 24 varies over its length. Resultantly, a stiffness of the first conical portion 24 correspondingly varies. In the illustrated exemplary embodiment, the cross-sectional area of the first conical portion 24 is greatest proximate to the handle portion 12 of the stem 10 and is smallest proximate to the second conical portion 26. Thus, the first conical portion 24 is of a greater stiffness in the area proximate to the handle portion 12 and is of a lesser stiffness at the area proximate to the second conical portion 26. This feature of enhanced stiffness in the area proximate to the stem handle portion 12 provides the first conical portion 24 with a sufficient rigidity to enable proper insertion of the attachment portion 14 of the stem 10 into the earcanal. Yet, the reduced stiffness of the first conical 24 in the area proximate the second conical portion 26 allows the attachment portion 14 to bend when the stem 10 is inserted into the earcanal thus permitting the stem to conform to the natural contour and curvature of the earcanal. Particularly, the reduced thickness of the first conical portion 24 at the second conical portion 26 acts as a hinge point or point of articulation which allows the second conical portion 26 and the front end 28 to pivot and articulate relative to the first conical portion 24 and the handle portion 12 of the stem 10. Thus, as the attachment portion 14 enters the earcanal, the attachment portion 14 is configured to articulate about the area of reduced cross-sectional area of the first conical portion 24 proximate to the second conical portion 26.

The front end 28 of the stem attachment portion 14, as mentioned, comprises a generally cylindrical member which extends from the second conical portion 26 to a terminable end of the earplug stem 10. This front end 28 comprises a reduced stiffness such that the front end 28 is capable of articulating during insertion of the stem 10 into the earcanal. This articulation allows the insertion portion 14 of the stem 10 to easily follow the contour and curve of the earcanal during earplug insertion. Thus, a sufficient depth of insertion may be achieved to provide optimized occlusion while providing the wearer with enhanced comfort properties.

The second conical portion 26 has a stiffness greater than that of the first conical portion 24 and greater than that of the front end 28. This enables the attachment portion 14 of the stem 10 to articulate at at least two points: (1) an area of the first conical portion 24 proximate to the second conical portion 26; and (2) an area of the front end 28 proximate to the second conical portion 26. That is, in a sense, the more rigid second conical portion 26 serves as a joint about which the first conical portion 24 and/or the front end 28 may articulate and pivot. Also, as discussed further herein in detail, the second conical portion is configured to be received and retained within a sound attenuating portion of a resulting earplug. Particularly, the second conical portion 26 is configured to attain a friction fit within the sound attenuating portion.

FIGS. 6-10 show the earplug 50 having the sound attenuating element 52 attached to the stem 10. Here, by way of example, the sound attenuating element 52 is shown as comprising a plurality of rearwardly facing semi-hemispherical flanges 54. Three such flanges 54 are shown. Of course, the earplug 50 may include more or less of the flanges 54 (e.g., four or more flanges, two flanges, a single flange, etc., see FIGS. 14-18 and 20 for an alternate embodiment). A base 56 of the sound attenuating element is disposed partly on the proximate portion 16 of the stem 10. Here, the sound attenuating element 52 may be formed of a thermoplastic elastomer (TPE), or any suitable compressible material. The sound attenuating element 52, for example, may be similar or identical to that disclosed in U.S. Pat. No. 4,867,149, issued on Sep. 19, 1989, the contents of which are herein incorporated by reference in their entirety.

The sound attenuating element 52 may be pre-molded and then is preferably affixed to the stem 10 by a friction/snap fit. In such embodiment, the attenuating element 52 is formed with a receptacle at its interior generally configured to receive and retain the attachment portion 14 of the stem 10. As discussed in detail below, the receptacle may have a cross-sectional area smaller than that of the attachment portion 14 of the stem 10 such that the friction fit is establish upon inserting the stem 10 into the receptacle. Additionally, the attachment features 24, 26, 28 of the attachment portion 14 may be configured to mate or create a snap-fit with the interior of the sound attenuating element 52 at the receptacle. That is, the portion 14 and the receptacle can include interlocking features such as male and female elements, etc.

Figure 11:
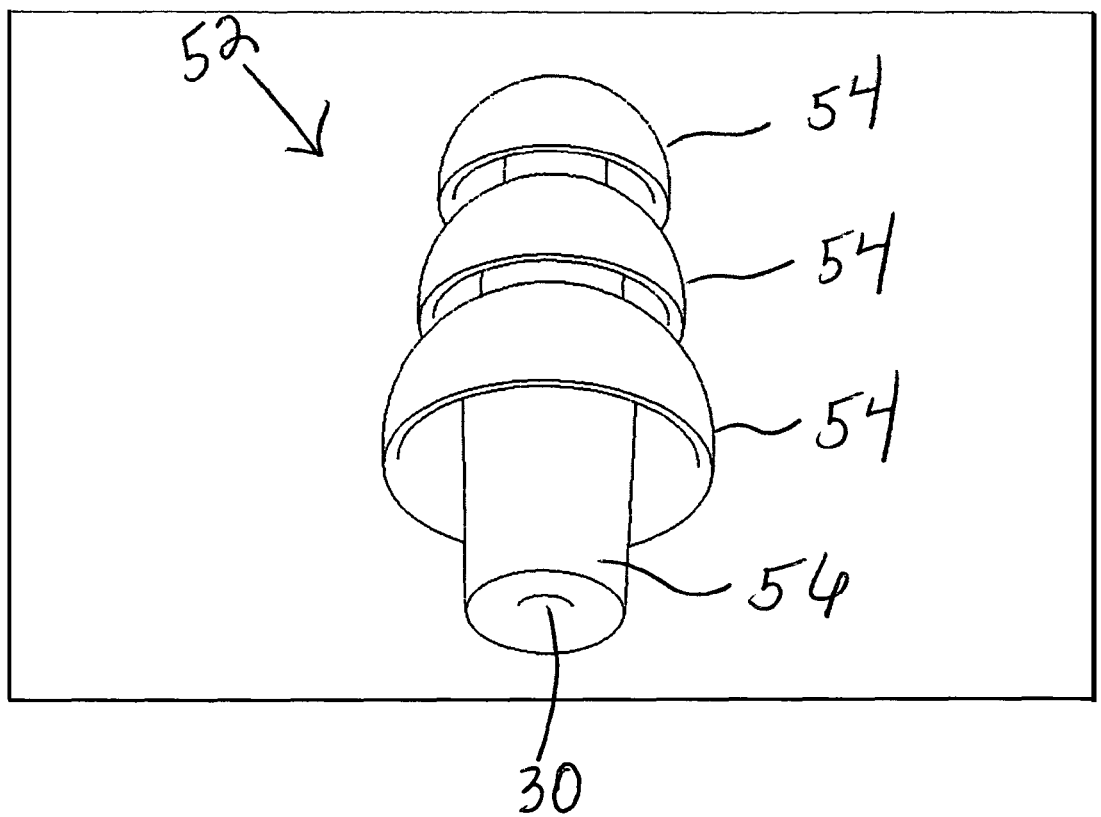
FIG. 11 is a perspective view of an attenuating portion of the earplug of FIGS. 6-10.
Figure 12:
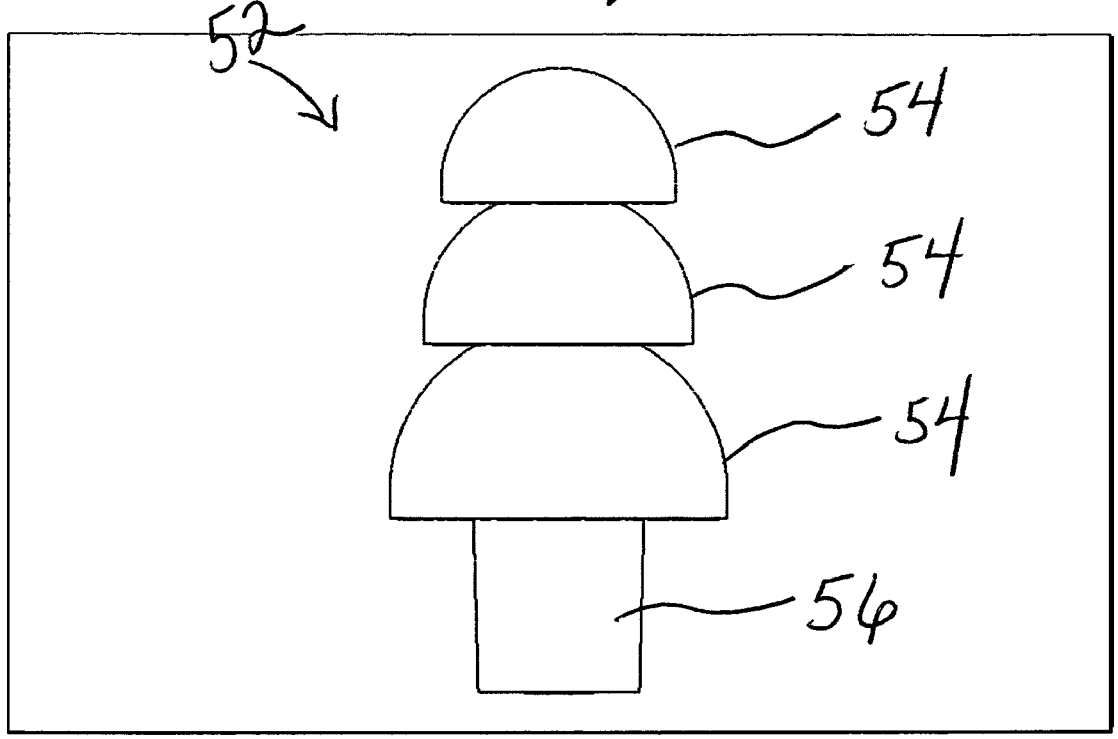
FIG. 12 is a side elevation view thereof.
Figure 13:
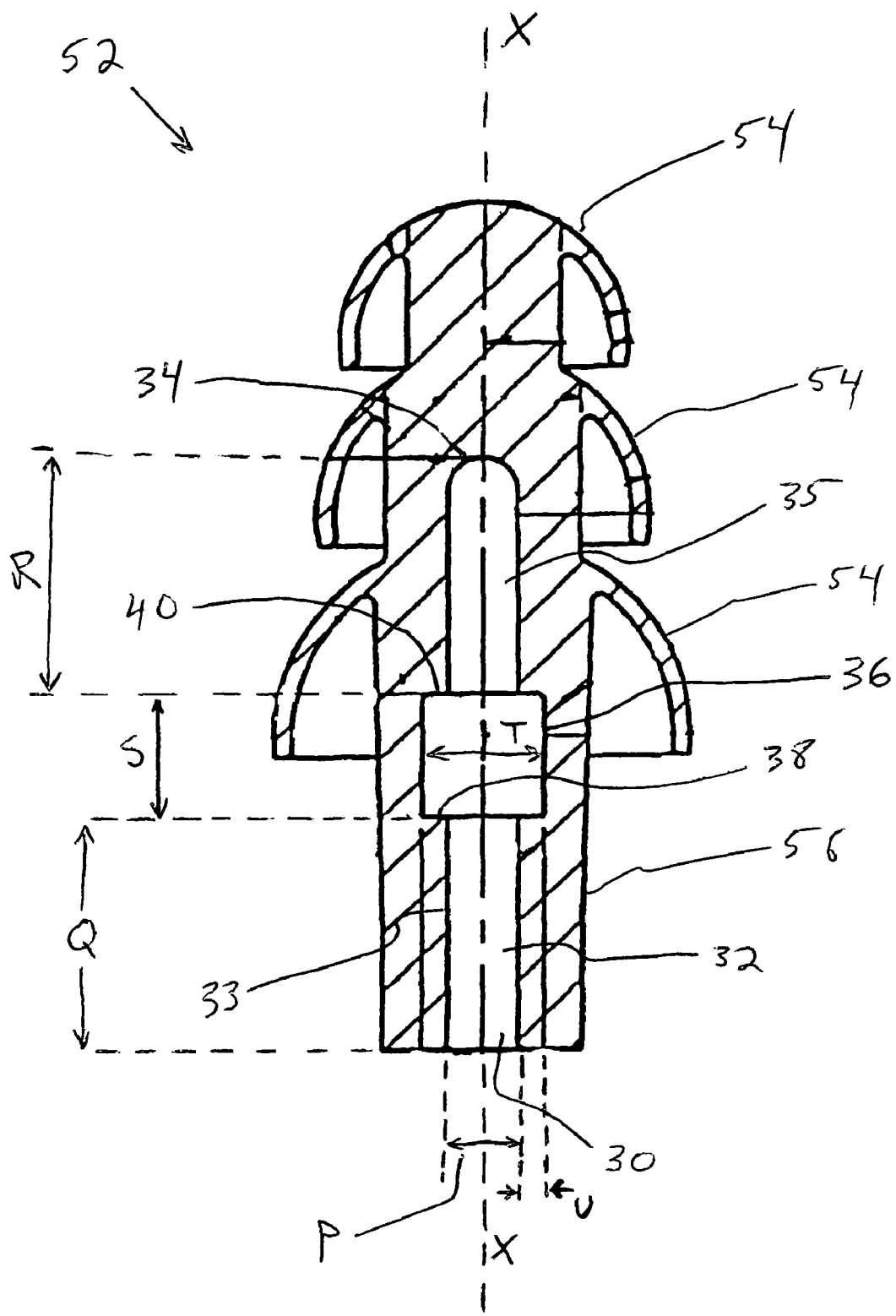
FIG. 13 is a cross-section view thereof.
Figure 14:
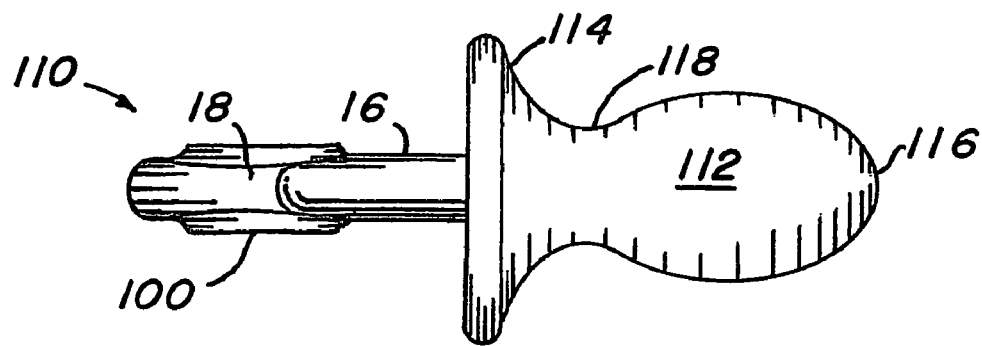
FIG. 14 is a side view of an earplug in another embodiment of the invention having the stem of FIGS. 1-5.
Figure 15:
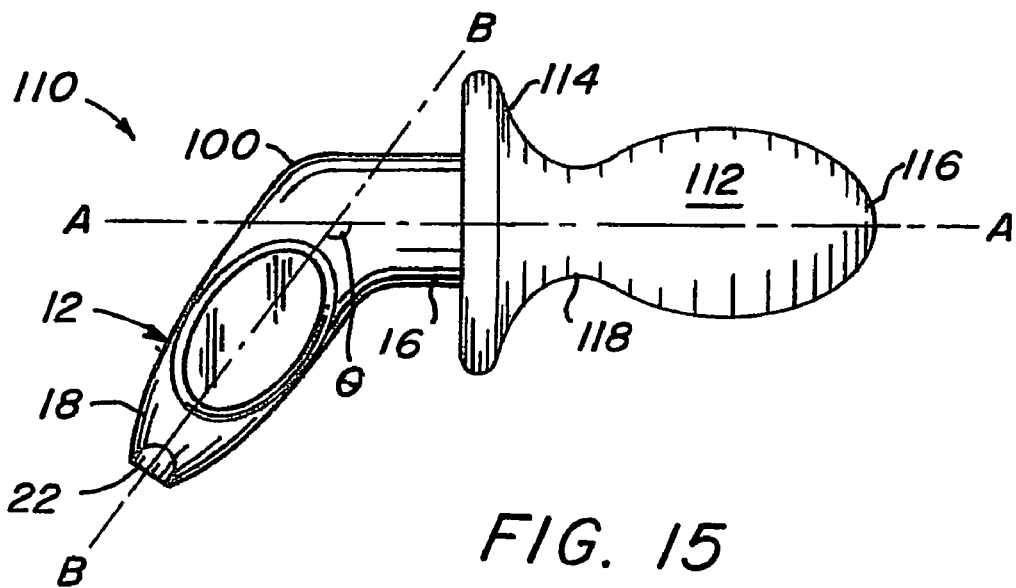
FIG. 15 is a top view thereof.
Figure 16:
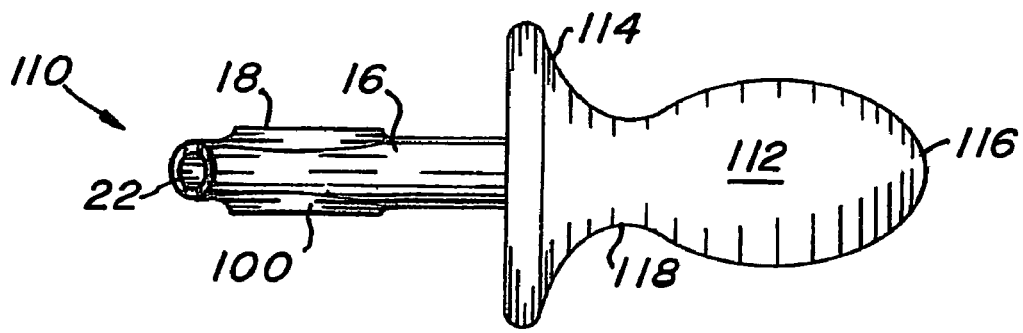
FIG. 16 is a bottom view thereof.
Figure 17:
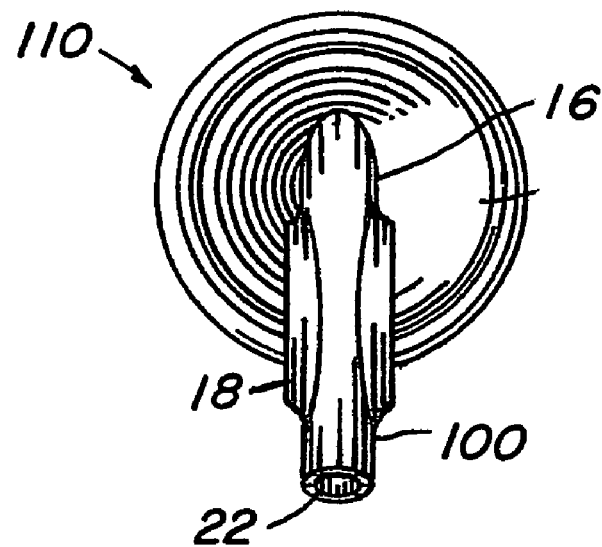
FIG. 17 is a rear view thereof.
Figure 18:
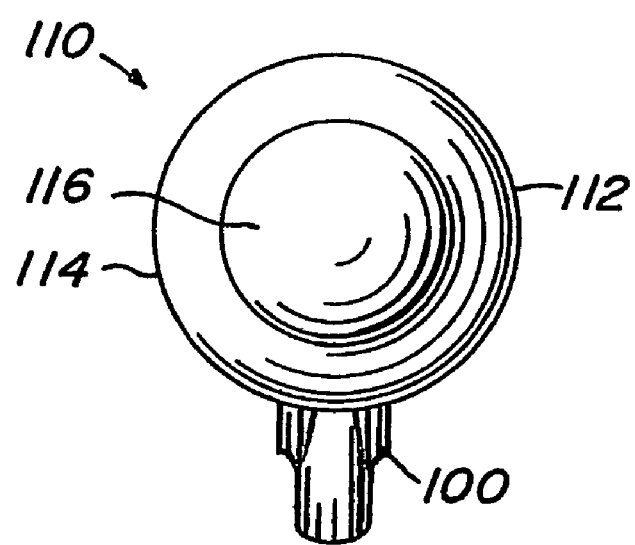
FIG. 18 is a front view thereof.

FIGS. 11-13 show various views of the sound attenuating element 52. The element 52 includes an aperture 30 which opens to a cavity 32 within the sound attenuating element 52. See, particularly, FIGS. 11 and 13. The cavity 32 includes a generally circular cross-section and extends inwardly along a longitudinal axis X-X of the sound attenuating element 52. The aperture 30 is disposed at a bottom surface of the base 56 and provides an opening between the cavity 32 and an exterior of the sound attenuating element 52. The cavity 32 extends through the base 56 and terminates at an area beneath one of the flanges 54, particularly, beneath a middle-most flange 54 as shown in FIG. 13. The cavity 32 includes a rounded area 34 at the point of termination of the cavity 32. The rounded area may be hemispherical, semi-hemispherical, or otherwise curved or angled as desired.

The cavity 32 includes a chamber 36 disposed about mid-length along the cavity 32. The chamber 36 is essentially a portion of the cavity 32 having a greater cross-sectional width than the remaining portions of the cavity 32. In this exemplary embodiment, the chamber 36 includes a circular cross-section greater than that of the cavity 32. The chamber 36 is particularly configured and disposed to receive and retain the second conical portion 26 of the stem 10, as will be further discussed herein. The chamber 36 extends along the axis X-X of the sound attenuating element 52 and is disposed generally concentric with the cavity 32. That is, the chamber 36 is disposed between a rearward portion 33 and a forward portion 35 of the cavity 32. The chamber 36 includes a first seat 38 which extends around one end of the chamber 36 proximate to the rearward portion 33 of the cavity 32. The chamber 36 further includes a corresponding second seat 40 disposed at the interface of the chamber 36 and the forward portion 35 of the cavity 32.

As mentioned, the cavity 32 and the chamber 36 are particularly configured and disposed to receive and retain the attachment portion of the 14 of the stem 10. That is, the attachment portion 14 is designed to mate and engage with the cavity 32 and chamber 36 such that the sound attenuating element 52 is fixedly attached to the stem 10 without the use of adhesives, welding, bonding, etc. Instead, a reliable friction-fit and/or snap-fit is established between the attenuating element 52 and the attachment portion 14 of the stem 10.

When the attachment portion 14 of the stem 10 is fully inserted within the cavity 32, the first conical portion 24 is disposed within the rearward portion 33 of the cavity 32 nearest the aperture 30, the second conical portion 26 is disposed within the chamber 36, and the front end 28 of the attachment portion 14 is disposed within forward portion 35 of the cavity 32 nearest the rounded area 34. See, FIGS. 1 and 13.

The cavity 32 includes a width P which is equal to or less than the widths A' and F of the first conical portion 24 and the front end 28, respectively. For example the width P is approximately less than or equal to about 0.150 inch. More particularly, the width P is about 0.050 inch to about 0.100 inch and is preferably about 0.080 inch. The rearward and forward portions 33, 35 of the cavity 32 include a length sufficient to receive and retain the relevant portions of the attachment portion 14 of the stem 10. For example, the rearward portion 33 of the cavity 36 includes a length Q of about 0.250 inch to about 0.300 inch and preferably of about 0.280 inch. The forward portion 35 of the cavity 32 includes a length R of about 0.200 inch to about 0.300 inch and preferably of about 0.300 inch. The forward portion 35 of the cavity 32 includes the rounded area 34 to receive a tip of the front portion 28 of the stem attachment portion 14 because this tip may be correspondingly rounded or may angled, etc., or may include protuberances, screw threads, etc.

The chamber 36, as described, is a substantially cylindrical orifice disposed along the cavity 32 between the forward and rearward portions 33 and 35 thereof. The chamber 36 is shaped and dimensioned to receive and retain the second conical portion 26. In this embodiment of the invention, the chamber 36 includes a circular cross-section equal to or less than that of the second conical portion 26. For example, the chamber may include a width T of less than or equal to about 0.200 inch. For example, the width T may be about 0.160 inch to about 0.120 inch and, more preferably, may be about 0.140 inch. A length S of the chamber 36 is of sufficient dimension to receive the length D of the second conical portion 26. For example, the length S may be about 0.120 inch to about 0.160 inch and, more preferably, is about 0.145 inch.

Notably, the disposition of the chamber 36 relative to the reward and forward portions 33 and 35 of the cavity 32 creates the first and second seats 38 and 40, respectively, both having a dimension U of about 0.040 inch to about 0.080 inch and, more preferably, of about 0.060 inch.

As mentioned, when the sound attenuating element 52 is properly mated with the attachment portion 14 of the stem 10, the second conical portion 26 is disposed within the chamber 36. In this configuration, the width B' of the second conical portion 26 is disposed adjacent to and engages against the seats 38 of the chamber 36. Because the dimension B' of the portion 26 is generally and preferably greater than the width T of the chamber 36, the second conical portion 26 is held fixedly and is retained within the chamber 36. In this way, the attachment portion 14 of the stem 10 is essentially locked within the interior of the sound attenuating element 52 thus forming the earplug 50.

As discussed herein, the sound attenuating element 52 is made of a flexible, stretchable elastomer material. Accordingly, the portions of the attenuating element 52 which delimit the chamber 32 are capable of stretching around the first conical portion 24 and the front end 28 when such are disposed, respectively, within the rearward portion 33 and the forward portion 35 of the cavity 32.

Assembly of the earplug 50 is commenced by first inserting the front end 28 of the stem attachment portion 14 into the aperture 30 disposed at the base 56 of the sound attenuating element 52. The front end 28 is passed into the rearward portion 33 of the cavity 32. As the attachment portion 14 is moved further into the cavity 32, the second conical portion 26 engages the sound attenuating element 52 proximate to the aperture 30.

Typically, as discussed above, the width B' of the second conical portion 26 is greater than the width P of the cavity. Accordingly, the second conical portion 26 resists forward movement of the attachment portion 14 into the cavity 32. However, the tapered shape of the frustum forming the second conical portion 26 and the stretchable nature of the sound attenuating element 52 combine to allow entry of the portion 26 into the rearward portion 33 of the cavity 32. That is, a width of the second conical portion 26 opposite from the width B' is less than the width B' and is generally less than the width P of the cavity 32. In this way, a forward end of the second conical portion 26 may enter the cavity 32. Then, as the attachment portion 14 is pressed further into the cavity 32, the angled sides of the second conical portion 26 uniformly expand the sound attenuating element 52 about the rearward portion 33 of the cavity 32 until the portion 26 is fully disposed within the rearward portion 33. Generally, at this point the front end 28 enters and passes through the chamber 36. Then, the attachment portion 14 is pressed further into the cavity 32 until the second conical portion 26 is received within the chamber 36.

As mentioned, as the width B' of the second conical portion 26 passes through the rearward portion 33 of the cavity 32, the proximate portions of the sound attenuating element 52 are pressed outwardly to accommodate said passage. When the width B' engages the first seat 38 of the chamber 36, the seat 38 may yield to the outward pressure exerted by the width B', such that the second conical portion 26 is rapidly positioned within the chamber 36. This rapid positioning defines the snap-fit feature mentioned above with respect to the attenuating element 52 and the stem 10. That is, to assemble the earplug 50, the attachment portion 14 of the stem 10 is essentially pressed into the cavity 32 of the attenuating element 52 until the second conical portion 26 snaps into, i.e., locks into place and is fully received within, the chamber 36. This snap-fit feature provides a tactile indication to the assembler that the stem 10 is properly mated within the sound attenuating element 52.

As noted, the length D of the second conical portion 26 is generally greater than the length S of the chamber 36. Thus, upon entry of the second conical portion 26 into the chamber 36, areas of the sound attenuating element 52 proximate the chamber 36 are forced to expand. This expansion results naturally in a compressive reaction force which acts upon the second conical portion 26 and serves to hold the portion 26 firmly and securely within the sound attenuating element 52.

When disposed within the chamber 36, the width B' of the second conical portion 26 buts the seat 38. Because the width B' is greater than the width P delimited by the seat 38 and the rearward portion 33 of the cavity 32, the attachment portion 14 of the stem 10 resists backward movement relative to the sound attenuating element 52. That is interaction of the second conical portion 26 and the seat 38 prevents the attachment portion 14 from withdrawing from the cavity 32. In this way, the stem 10 is essentially locked within the sound attenuating element. That is, the stem 10 is securely fixed therein without requiring the use of adhesives or without having the attenuating element 52 formed directly on or otherwise bonded directly to the stem 10.

Upon entry of the second conical portion 26 into the chamber 36, the front end 28 of the stem attachment portion 14 is placed within the forward portion 35 of the cavity 32. Correspondingly, at this point, the first conical portion 24 enters and becomes fully disposed within the rearward portion 33 of the cavity 32. As discussed above, the width A' of the first conical portion 24 is generally greater than the width P of the cavity 32. Thus, upon insertion of the first conical portion 24 into the rearward portion 33 of the cavity 32, proximate areas of the attenuating element 52 stretch outwardly to accommodate the portion 24. This creates a pressure upon the first conical portion 24 which assists in holding the portion 24, and the entire attachment portion 14, firmly within the cavity 32. This contributes to the friction-fit existing between the stem 10 and the sound attenuating element 52.

In the illustrated exemplary embodiment of the invention, the second conical portion 26 of the attachment portion 14 of the stem 10 is disposed at an approximate mid-point of a longitudinal length of the sound attenuating element 25 when the stem 10 is disposed therein. See, e.g., FIG. 13. This creates an advantageous point of articulation at an area generally midway between a front and rear of the sound attenuating element 25. The positioning of the second conical portion 26 within the sound attenuating element 25 corresponds to an approximate first bend of a typical earcanal. Thus, the earplug 50 is particularly suited for being inserted into the earcanal and traversing this first bend in the earcanal due to the articulation property of the attachment portion 14 of the stem 10. This allows easy insertion of the earplug 50 to a sufficient depth within the earcanal and results in a comfortable occlusion of the earcanal once inserted. The disposition of the second conical portion 26 within the sound attenuating element 52 further ensures that the approximate center of mass of the element 25 (in combination with the underlying stem attachment portion 14) lies in front of the handle portion 12 of the stem 10. This results in the wearer grasping earplug 50 via the handle portion 14 at position behind the center of mass of the inserted portion of the earplug. Thus, the earplug 50 is readily manipulated and easily driven into the earcanal.

The sound attenuating element 52 has been discussed and shown herein by way of example as including the three semi-hemispherical flanges 54. It shall be appreciated that the broad scope of the invention contemplates a sound attenuating element of any one of a variety of configurations and/or constructions. For example, in another embodiment of the invention shown in FIGS. 14-18 and 20, an earplug 110 is provided including a stem 100 and a sound attenuating element 112. The stem 100 and sound attenuating element 112 are similar in many respects to the stem 10 and attenuating element 52, respectively, which are discussed above. Features which are consistent between the various embodiments of the invention discussed herein are indicated by consistent reference numerals and, for sake of brevity, are not reintroduced or discussed in substantive detail.

The stem 100 includes the handle portion 12 extending along the axis B-B and the attachment portion 14 extending along the axis A-A, where the axes intersect at the angle θ. The attenuating element 112 is affixed to the stem 100 over the attachment portion 14 (not shown) in similar fashion as described above with respect to the earplug 10. That is, the attenuating element 112 includes a channel and receptacle disposed and configured to receive and retain the attachment portion 14 of the stem 100 in snap-fit and/or friction-fit arrangement. See discussion above pertaining to the earplug 10.

A rear 114 of the sound attenuating element 112 proximate to the handle portion 12 of the stem 100 is essentially an outwardly extending flange element, as shown in the drawings, which is configured to seal the ear canal of a wearer when the earplug 110 is inserted therein. A front 116 of the sound attenuating element 112 includes a rounded shape, such as a semi-hemispherical, semi-elliptical, etc. shape, in order to facilitate insertion of the earplug 110 into the ear canal. The sound attenuating element 112 further includes a tapered portion 118 disposed between the front 116 and rear 114. The tapered portion 118 is an area of reduced cross-sectional area which extends generally in a middle portion of the sound attenuating element 112. Of course, the element 112 may alternatively include a substantially cylindrical shape of generally uniform cross-sectional diameter. Still further, the sound attenuating element 112 may comprise spherical shape, a rearwardly extending flange shape, or any desired shape and/or configuration.

Figure 20:
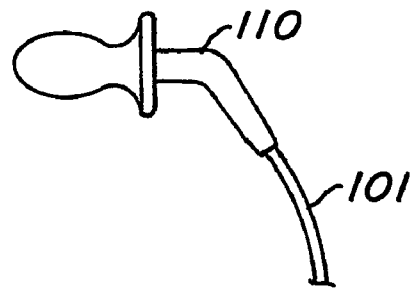
FIG. 20 is a side elevation view of an earplug according to FIGS. 14-18 having a cord attached thereto.

Like the earplug 50, the earplug 110 includes the aperture 22 formed in the stem 100 for receipt and retention of a cord 101, as shown in FIG. 20. The cord 101 is configured to be similarly attached to a second earplug 110 to thus form a corded pair of earplugs 110. The cord 101 may be friction fit within the aperture 22 or bonded to or molded therewith.

An interior (not shown) of the sound attenuating element 112 is substantially similar to that of the sound attenuating element 52. That is, the attenuating element 112 includes the cavity 32 and the chamber 36 disposed between rearward and forward portions 33 and 35 of the cavity 32. As in the earplug 10, the cavity 32 and chamber 36 are particularly disposed, configured, and dimensioned within the sound attenuating element 112 to receive and retain the attachment portion 14 of the stem 110 in order to provide the friction-fit and/or snap-fit between the element 112 and the stem 110. Reference is made herein to the above-provided descriptions.

The sound attenuating element 112 of the earplug 110 is formed preferably of a compressible, resilient slow-recovery foam material such as polyvinylchloride (PVC) or polyurethane. For example, the sound attenuating element 112 may be composed of a material as that described in U.S. Pat. No. Re. 29,487 issued on Dec. 6, 1977, the contents of which are herein incorporated by reference in their entirety.

The handle portion 12 of the earplugs 50, 110 described herein may be substantially cylindrical in shape, having a generally consistent cross-sectional diameter across its length. Alternatively, the handle portion 12 can include cross-sections of variable diameter such that an area(s) of the handle 12 tapers inwardly and/or outwardly. In another embodiment, the handle portion includes a rectilinear or elliptical cross-section of consistent or variable cross-sectional area. Further, the handle portion 12 may include a combination of some or all of these configurations and/or further configurations as desired.

The handle portion 12 of the invention has thus far been described as being composed of intersecting substantially linear proximate and distal portions 16 and 18, respectively. In another embodiment of the invention, the handle portion 12 of the stem 10, 100 extends in a curvilinear fashion from the sound attenuating element 52, 112. That is, in such embodiment, the handle portion is at least partially rounded such that the portion 12 curves away from the longitudinal axis A-A of the attachment portion 14 and of the sound attenuating element 52, 112.

Figure 21:
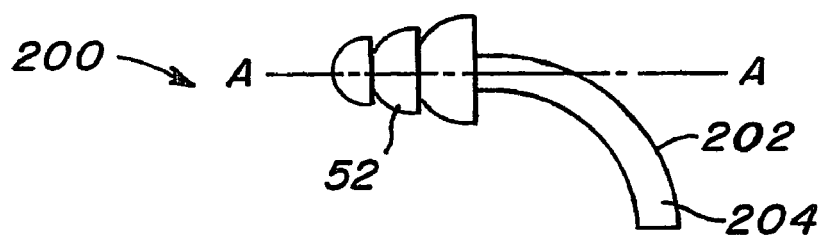
FIGS. 21-24 are side views of earplugs in other embodiments of the invention.
Figure 22:
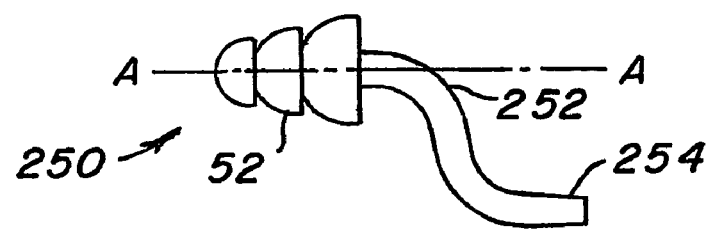

For example, FIG. 21 shows an earplug 200 having the sound attenuating element 52 attached to a stem 202. The stem 202 includes the attachment portion 14 (not shown) and a curved handle 204. The handle 204 traces a curve which, for example, may be a portion of a radius of a circle, a portion of an ellipse, or any other desired curve. FIG. 22 shows an earplug 250 in another embodiment of the invention. The earplug 250 includes a stem 252 which includes the attachment portion 14 (not shown) affixed to the sound attenuating element 52 and which further includes a curvilinear handle 254 extending therefrom. The handle 254 traces a substantially serpentine pattern, i.e., an approximately S-shaped pattern.

Figure 23:
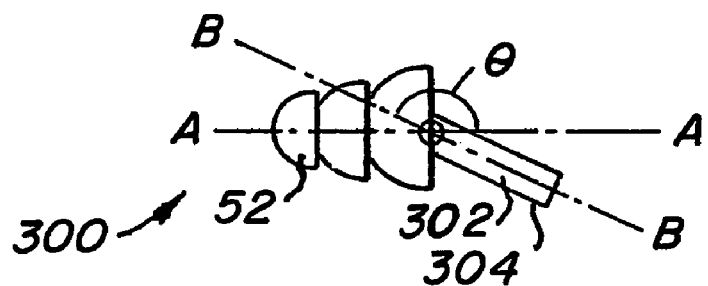

FIG. 23 shows an earplug 300 in another embodiment of the invention. The earplug 300 includes the sound attenuating element 52 and a stem 302 extending therefrom. The stem 302 includes the attachment portion 14 (not shown) and a handle portion 304 extending from the attenuating element 52. The handle portion 304 extends in a substantially linear fashion along the axis B-B which forms the angle e with the axis A-A of the sound attenuating element 52. That is, the handle portion 304 is similar to the handle portion 14 of the stem 10 except that, here, the handle 304 does not include a proximate portion collinear with the attenuating element as does the stem 10. To the contrary, the entirety of the handle 304 extends angularly relative to the sound attenuating portion.

Figure 24:
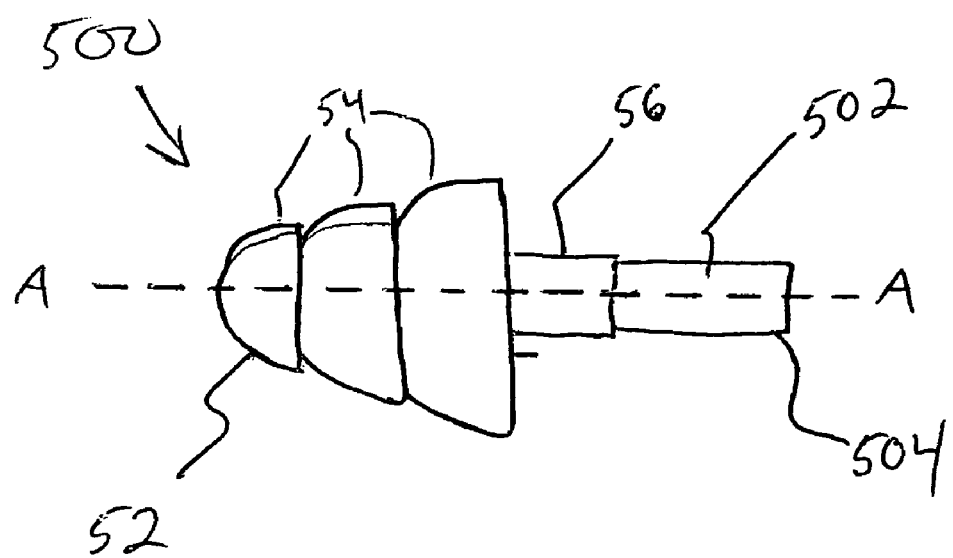

Another alternate embodiment of the invention is shown in FIG. 24. Therein, an earplug 500 includes the sound attenuating element 52 attached to a stem 502 having a handle portion 504. Here, the handle portion 504 and attachment portion 14 (not shown) are collinear and extend along the axis A-A of the attenuating element 52.

In all of these alternate embodiments, the stems 202, 252, 302, and 502 are attached to the sound attenuating elements 52 by way of the above-discussed interaction between the cavity 32 and chamber 36 of the sound attenuating elements 52 and the locking features 24, 26, and 28 of the attachment portions 14 of the respective stems. That is, each stem 202, 252, 302, and 502 includes the first conical portion 24, the second conical portion 26, and the front end 28 which are configured to mate securely with the cavity 32 and the chamber 36 as discussed above. Thus, the earplugs 200, 250, 300, and 500 are assembled by first manufacturing the respective stems 202, 252, 302, and 502 and the sound attenuating elements 52 and then inserting the front end 28 of each stem into the particular cavity 32 and pressing until the second conical portion 26 is fixedly disposed in the chamber 36.

It is noted that the stem handles 204, 254, and 304 of the earplugs 200, 250, and 300, respectively, are shown in the drawings as having a circular cross-section which is of consistent shape and size across a length of the handle. Alternatively, of course, the handles 204, 254, 304 may comprise a variably shaped and/or sized cross-section. The handles 204, 254, 304 can additionally and/or alternatively comprise the handling area 20 and the aperture 22 for receipt and retention of a cord.

The sound attenuating elements 52, 112 discussed herein may be of the push-in type, the roll-down type, or the partial roll-down type. That is, the sound attenuating elements 52, 112, in one embodiment, are inserted into the ear canal by simply placing the element at the entrance of the canal and pushing inwardly on the handle portion 12 of the stem 10, 100. In another embodiment, the sound attenuating element 52, 112 is rolled between the fingers in order to fully compress the element 52, 112 against the attachment portion 14 of the stem 10, 100 prior to insertion of the element 52, 112 into the ear canal. In a further embodiment, the attenuating element 52, 112 is compressed only partially prior to insertion.

The various stems 10, 100, 202, 252, 302, and 502 described herein may be formed of a plastic or rubber material and may be formed through a molding process, and particularly, by an injection molding process.

The features of the stems 10, 100, 202, 252, 302, and 502 responsible for locking the stems within the interior of the sound attenuating elements 52 and 112 have been described herein by way of example only. That is, the first conical portion 24, and the second conical portion 26, and the front end 28 and the corresponding cavity 32, chamber 36, and rounded portion 34 are merely illustrative of the broad inventive concept of providing an earplug composed of a stem and an attenuating element which are securely attachable without use of an adhesive of other bonding techniques. For example, the stem of the invention may comprise any type of protrusion without limitation configured to be received and retained within a cavity of the sound attenuating element. Such protrusion may be curvilinear or rectilinear in shape or a combination thereof. The protrusion, for example, may include a spherical or semi-spherical shape and the cavity may include a corresponding spherical or semi-spherical shape of a slightly smaller dimension than that of the protrusion such that the protrusion may be lockingly received in a friction-fit within the cavity. Alternatively, the protrusion may be substantially pyramidal, etc. and shape and the corresponding cavity may be similarly shaped to provided the desired mating of the stem and attenuating element. The stem protrusion may have a smooth outer surface (as seen in the second conical portion 26 described herein) or may include additional locking features such as ridges, ribs, protuberances, barbs, screw threads, etc. to further provide locking engagement between the stem and the attenuating element. Additionally and/or alternatively, the portions of the sound attenuating element which form the cavity may include said additional locking features.

Accordingly, the invention results in a hearing protection device, particularly an earplug, which includes a soft compressible sound attenuating element and a more rigid stem where the stem is attached to the sound attenuating element by locking features disposed on the stem and/or on the sound attenuating element such that adhesives, bonding, welding, etc., are not required in assembling the earplug. The resulting earplug includes a stem which is sufficiently rigid to facilitate insertion of the earplug into the earcanal by which remains sufficiently pliable to bend within the earcanal according to the natural contours of the inner ear. This stem is easily attachable to the soft compressible attenuating element to provide an earplug which is very comfortable to the wearer, easily insertable, and which may be readily assembled at a respectively lower cost without the use of adhesives, bonding or welding techniques, etc.

Dimensions and materials identified in this description and the attached Figures are for illustration purposes only and may vary depending upon the intended application in accordance with the teachings of the present invention. The present invention is not intended to be limited to the specific features of the Figures even though the invention encompasses the same.

Furthermore, it will be apparent to those skilled in the art that, while exemplary embodiments have been shown and described, various modifications and variations can be made to the present apparatus and method disclosed herein without departing from the spirit or scope of the invention. Accordingly, it is to be understood that the various embodiments have been described by way of illustration and not limitation.

The invention claimed is:

1. An hearing protection device, comprising:
    a stem;
    a protrusion formed on the stem;
    an articulation point formed on the stem; and
    a sound attenuating element including a cavity;
    wherein the protrusion is disposed in locking engagement within the cavity to releasably attach the stem to the sound attenuating element; and
    wherein the stem is configured to at least partially articulate about the articulation point.

2. The hearing protection device of claim 1, wherein the articulation point comprises an portion of the stem having a reduced cross-sectional area.

3. The hearing protection device of claim 2, wherein the portion of reduced cross-sectional area is disposed proximate to the protrusion.

4. The hearing protection device of claim 1, wherein the stem includes a serially decreasing cross-sectional diameter in a direction toward the protrusion and wherein an portion of least cross-sectional area delimits the articulation point proximate to the protrusion.

5. The hearing protection device of claim 1, wherein the stem comprises a substantially conical shape having an end disposed proximate to the protrusion, wherein the end comprises a portion of the stem of reduced cross-section, and wherein the end delimits the articulation point.

6. The hearing protection device of claim 1, wherein the stem comprises a conical portion including an end disposed adjacent to the protrusion, the stem further comprising a cylindrical portion extending from the protrusion opposite from the conical portion.

7. The hearing protection device of claim 6, wherein the end is an area of the conical portion having a reduced cross-sectional area, said end delimiting the articulation point.

8. The hearing protection device of claim 6, wherein the cavity of the sound attenuating element is configured to receive and releasably retain the cylindrical portion and at least part of the conical portion.

9. The hearing protection device of claim 8, wherein the protrusion is disposed at approximately a midpoint of a length of the sound attenuating element such that the stem and the sound attenuating element are articuable about said midpoint.

10. The hearing protection device of claim 6, wherein the protrusion comprises a conical shape having a base adjacent to the conical portion, said end being adjacent to the cylindrical portion.

11. The hearing protection device of claim 1, wherein the stem comprises an attachment portion having the protrusion formed thereon and configured to be disposed within the sound attenuating element.

12. The hearing protection device of claim 11, wherein the stem further comprises a handle portion including grip features to facilitate handling the stem.

13. The hearing protection device of claim 12, wherein the attachment portion extends generally along a first longitudinal and the handle portion extends generally along a second longitudinal axis, wherein said first and second longitudinal axes are not collinear.

14. The hearing protection device of claim 13, wherein the second longitudinal axis extends from the first longitudinal axis at an angle of approximately less than or equal to 125 degrees.

15. The hearing protection device of claim 14, wherein the attachment portion comprises an area of reduced cross-section disposed proximate to the protrusion, wherein said area of reduced cross-section delimits said articulation point.

16. The hearing protection device of claim 14, wherein the attachment portion comprises a conical portion including an end disposed adjacent to the protrusion, the attachment portion further comprising a cylindrical portion extending from the protrusion opposite from the conical portion, wherein, said end delimits the articulation point.

17. A hearing protection device, comprising:
    an elongated stem member including an attachment portion and a handle portion;
    a protrusion formed on the attachment portion of the stem member;
    an area of reduced stem member cross-sectional area delimited by the attachment portion proximate to the protrusion; and
    a sound attenuating element including a cavity formed at an interior thereof;
    wherein the attachment portion is disposed within the cavity;
    wherein the protrusion is disposed within the cavity in locking engagement with a mating element of the sound attenuating element to releasably attach the stem member to the sound attenuating element;
    wherein the area of reduced stem member cross-sectional area delimits an articulation point of the stem member; and
    wherein the stem member and the sound attenuating element disposed thereon are configured to at least partially articulate about the articulation point.

18. The hearing protection device of claim 17, wherein the attachment portion extends generally along a first longitudinal and the handle portion extends generally along a second longitudinal axis, wherein said first and second longitudinal axes are not collinear.

19. The hearing protection device of claim 18, wherein the second longitudinal axis extends from the first longitudinal axis at an angle of approximately less than or equal to 125 degrees.

20. The hearing protection device of claim 17, wherein the attachment portion comprises a conical portion including an end disposed adjacent to the protrusion, the attachment portion further comprising a cylindrical portion extending from the protrusion opposite from the conical portion, wherein, said end delimits the area of reduced stem member cross-sectional area and the articulation point.

* * * * *

UNITED STATES PATENT AND TRADEMARK OFFICE
CERTIFICATE OF CORRECTION

PATENT NO. : 7,743,771 B2  Page 1 of 1
APPLICATION NO. : 11/584326
DATED : June 29, 2010
INVENTOR(S) : Robert N Falco It is certified that error appears in the above-identified patent and that said Letters Patent is hereby corrected as shown below:

Column 11
Line 35, delete "e" and insert -- θ --, therefor.

Column 13
Claim 9, delete "articuable" and insert -- articulable --, therefor.

Signed and Sealed this

Ninth Day of November, 2010

David J. Kappos
*Director of the United States Patent and Trademark Office*